US007626389B2

(12) United States Patent
Fiedler et al.

(10) Patent No.: US 7,626,389 B2
(45) Date of Patent: Dec. 1, 2009

(54) PET/MR SCANNER WITH TIME-OF-FLIGHT CAPABILITY

(75) Inventors: Klaus Fiedler, Vienna (AT); Jacobus A. J. M. Deckers, Eindhoven (NL); Thomas Frach, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/911,831

(22) PCT Filed: Mar. 28, 2006

(86) PCT No.: PCT/IB2006/050944

§ 371 (c)(1),
(2), (4) Date: Apr. 30, 2008

(87) PCT Pub. No.: WO2006/111869

PCT Pub. Date: Oct. 26, 2006

(65) Prior Publication Data

US 2008/0284428 A1 Nov. 20, 2008

Related U.S. Application Data

(60) Provisional application No. 60/674,033, filed on Apr. 22, 2005.

(51) Int. Cl.
*G01V 3/00* (2006.01)
(52) U.S. Cl. ........................ 324/309; 324/307
(58) Field of Classification Search .............. 324/307, 324/309
See application file for complete search history.

(56) References Cited

U.S. PATENT DOCUMENTS 4,939,464 A 7/1990 Hammer
5,532,489 A * 7/1996 Yamashita et al. ...... 250/363.03

(Continued)

FOREIGN PATENT DOCUMENTS

DE 3208178 A1 9/1983

(Continued)

OTHER PUBLICATIONS

Aull, B. F., et al.; Geiger-Mode Avalanche Photodiodes for Three-Dimensional Imaging; 2002; Lincoln Laboratory Journal; 13(2)335-350.

(Continued)

*Primary Examiner*—Louis M Arana

(57) ABSTRACT

In a combined scanner, a main magnet (20) and magnetic field gradient coils (28) housed in or on a scanner housing (12, 18) acquires spatially encoded magnetic resonances in an imaging region (14). Solid state radiation detectors (50, 50', 50") disposed in or on the scanner housing are arranged to detect gamma rays emitted from the imaging region. Time-of-flight positron emission tomography (TOF-PET) processing (52, 54, 58, 60, 62) determines localized lines of response based on (i) locations of substantially simultaneous gamma ray detections output by the radiation detectors and (ii) a time interval between said substantially simultaneous gamma ray detections. TOF-PET reconstruction processing (64) reconstructs the localized lines of response to produce a TOF-PET image. Magnetic resonance imaging (MRI) reconstruction processing (44) reconstructs the acquired magnetic resonances to produce an MRI image.

20 Claims, 6 Drawing Sheets

U.S. PATENT DOCUMENTS

| | | |
|---|---|---|
| 6,631,284 B2 | 10/2003 | Nutt et al. |
| 6,946,841 B2 * | 9/2005 | Rubashov .................. 324/318 |
| 2003/0090267 A1 | 5/2003 | Rubashov |
| 2005/0113667 A1 | 5/2005 | Schlyer et al. |
| 2006/0251312 A1 | 11/2006 | Krieg et al. |

FOREIGN PATENT DOCUMENTS

| | | |
|---|---|---|
| JP | 60105982 A | 6/1985 |
| JP | 02105641 A | 4/1990 |
| WO | 03003038 A1 | 1/2003 |
| WO | 2004111681 A1 | 12/2004 |
| WO | 2005019862 A1 | 3/2005 |
| WO | 2006071922 A2 | 7/2006 |
| WO | 2006119085 A2 | 11/2006 |

OTHER PUBLICATIONS

Buzhan, P., et al.; An Advanced Study of Silicon Photomultiplier; ICFA Instrumentation Bulletin, Moscow, Russia.

Georgievskya, E. A., et al.; The solid-state silicon photomultiplier for a wide range of applications; 2003; 17th Intl. Conf. on Photoelectronics and Night Vision Devices; Proc. of SPIE; vol. 5126; pp. 37-42.

Golovin, V., et al.; Novel type of avalanche photodetector with Geiger mode operation; 2004; Nuclear Instruments & Methods in Physics Research; A 518:560-564.

Pichler, B. J., et al.; Lutetium oxyorthosilicate block detector readout by avalance photodiode arrays for high resolution animal PET; 2004; Phys. Med. Biol.; 49:4305-4319.

Sadygov, Z. Y., et al.; Avalanche Semiconductor Radiation Detectors; 1996; IEEE Trans. on Nuclear Science; 43(3) 1009-1013.

Saveliev, V.; The recent development and study of silicon photomultiplier; 2004; Nuclear Instruments and Methods in Physics Research; A 535:528-532.

Shao, Y., et al.; Development of a PET Detector System Compatible with MRI/NMR Systems; 1997; IEEE Trans. on Nuclear Science; 44(3)1167-1171.

* cited by examiner

PET/MR SCANNER WITH TIME-OF-FLIGHT CAPABILITY

CROSS REFERENCE TO RELATED APPLICATIONS

This application claims the benefit of U.S. provisional application Ser. No. 60/674,033 filed Apr. 22, 2005, which is incorporated herein by reference.

DESCRIPTION

The following relates to the imaging arts. It finds particular application in medical imaging using a combination of positron emission tomography (PET) and magnetic resonance imaging (MRI).

Magnetic resonance imaging (MRI) combines high magnetic fields, magnetic field gradients, and radio frequency excitation pulses to generate and spatially encode magnetic resonances in a human patient or other imaging subject. The magnetic resonances are processed by a Fourier transform or other reconstruction process to decode the spatial encoding and produce a reconstructed image of the subject.

In positron emission tomography (PET), a positron-emitting radiopharmaceutical is administered to a human patient or other imaging subject. Each positron annihilation produces two oppositely directed gamma rays having energies of about 511 keV. The two gamma rays are detected by radiation detectors surrounding the imaging subject, defining a line of response (LOR). A multitude of such positron annihilation events define projection-like LOR data that can be reconstructed by filtered backprojection, iterative reconstruction, or another reconstruction technique to produce a reconstructed image.

MRI typically provides images with strong morphological features including soft tissue contrast. PET is typically used for functional imaging. The combination of MRI and PET has been recognized as having synergistic advantages. For example, the morphology elucidated by MRI can provide context for interpreting PET functional imaging. Unfortunately, operating an MRI has adverse effects on the operation of a nearby PET scanner. PET scanners generally employ scintillators to convert the gamma rays to bursts of light, and photomultiplier tubes (PMTs) to detect the scintillation events. PMTs are adversely affected by magnetic fields, thus making direct incorporation of PET scanner hardware into the high magnetic field environment of an MRI scanner problematic. Obtaining high quality PET images is difficult in general. Signal to noise ratio (SNR) is typically low because the radioactivity of the radiopharmaceutical is limited by patent exposure concerns. Additionally, PET images typically include image noise introduced by reconstruction processing of the LOR's to produce the reconstructed image. Heat and vibrations produced by the MR components can further increase image noise for PET systems operating in an MR environment.

The resolution in the PET images as well as the count rate capability of the PET scanner can be increased by using a higher density of radiation detectors. But, smaller detectors have lower radiation count rates and correspondingly have higher noise. Moreover, space is a valuable commodity in an MRI scanner bore, which already houses MR components such as a cryogenically cooled main magnet, a number of magnetic field gradient coils, steel shims and/or shim coils, radio frequency coils, and so forth.

The following contemplates improved apparatuses and methods that overcome the aforementioned limitations and others.

According to one aspect, an imaging system is disclosed. A magnetic resonance imaging scanner includes at least a main magnet and magnetic field gradient coils housed in or on a scanner housing. The magnetic resonance imaging scanner acquires spatially encoded magnetic resonances in an imaging region. A plurality of solid state radiation detectors disposed in or on the scanner housing are arranged to detect gamma rays emitted from the imaging region. Time-of-flight positron emission tomography (TOF-PET) processing is configured to determine localized lines of response based on (i) locations of substantially simultaneous gamma ray detections output by the solid state radiation detectors and (ii) a time interval between said substantially simultaneous gamma ray detections. Time-of-flight positron emission tomography (TOF-PET) reconstruction processing is configured to reconstruct the localized lines of response to produce a TOF-PET image. Magnetic resonance imaging (MRI) reconstruction processing is configured to reconstruct the acquired magnetic resonances to produce an MRI image.

According to another aspect, an imaging method is provided. Spatially encoded magnetic resonances are acquired from within an imaging region. Gamma rays emitted from the imaging region are detected. Localized lines of response are determined based on (i) locations of detections of substantially simultaneously detected gamma rays and (ii) a time interval between said detections of said substantially simultaneously detected gamma rays. The localized lines of response are reconstructed to produce a time-of-flight positron emission tomography (TOF-PET) image. The acquired spatially encoded magnetic resonances are reconstructed to produce a magnetic resonance imaging (MRI) image.

According to another aspect, an imaging system is disclosed. A magnetic resonance imaging scanner includes at least a main magnet and magnetic field gradient coils housed in or on a scanner housing. The magnetic resonance imaging scanner acquires spatially encoded magnetic resonances in an imaging region. A plurality of solid state radiation detectors disposed in or on the scanner housing are arranged to detect gamma rays emitted from the imaging region. A cooling system is thermally coupled with at least one of the main magnet and the magnetic field gradient coils to cool said at least one of the main magnet and the magnetic field gradient coils, and is additionally thermally coupled with the plurality of solid state radiation detectors to cool the solid state radiation detectors. Coincidence processing is configured to determine lines of response based on locations of substantially simultaneous gamma ray detections output by the solid state radiation detectors. Positron emission tomography (PET) reconstruction processing is configured to reconstruct the lines of response to produce a PET image. Magnetic resonance imaging (MRI) reconstruction processing is configured to reconstruct the acquired magnetic resonances to produce an MRI image.

One advantage resides in providing TOF-PET imaging data acquired by a PET/MR scanner which is amenable to reduced-noise reconstruction.

Another advantage resides in providing a PET/MR scanner generating high resolution PET images.

Another advantage resides in simplified construction of a PET/MR scanner.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a TOF-PET/MRI system employing solid state radiation detectors for the PET data acquisition.

FIG. 2 diagrammatically shows a cross-sectional view of one of the solid state radiation detectors which employs a silicon photomultiplier.

FIG. 3 diagrammatically shows a plan view of the silicon photomultipliers.

Figure 1:
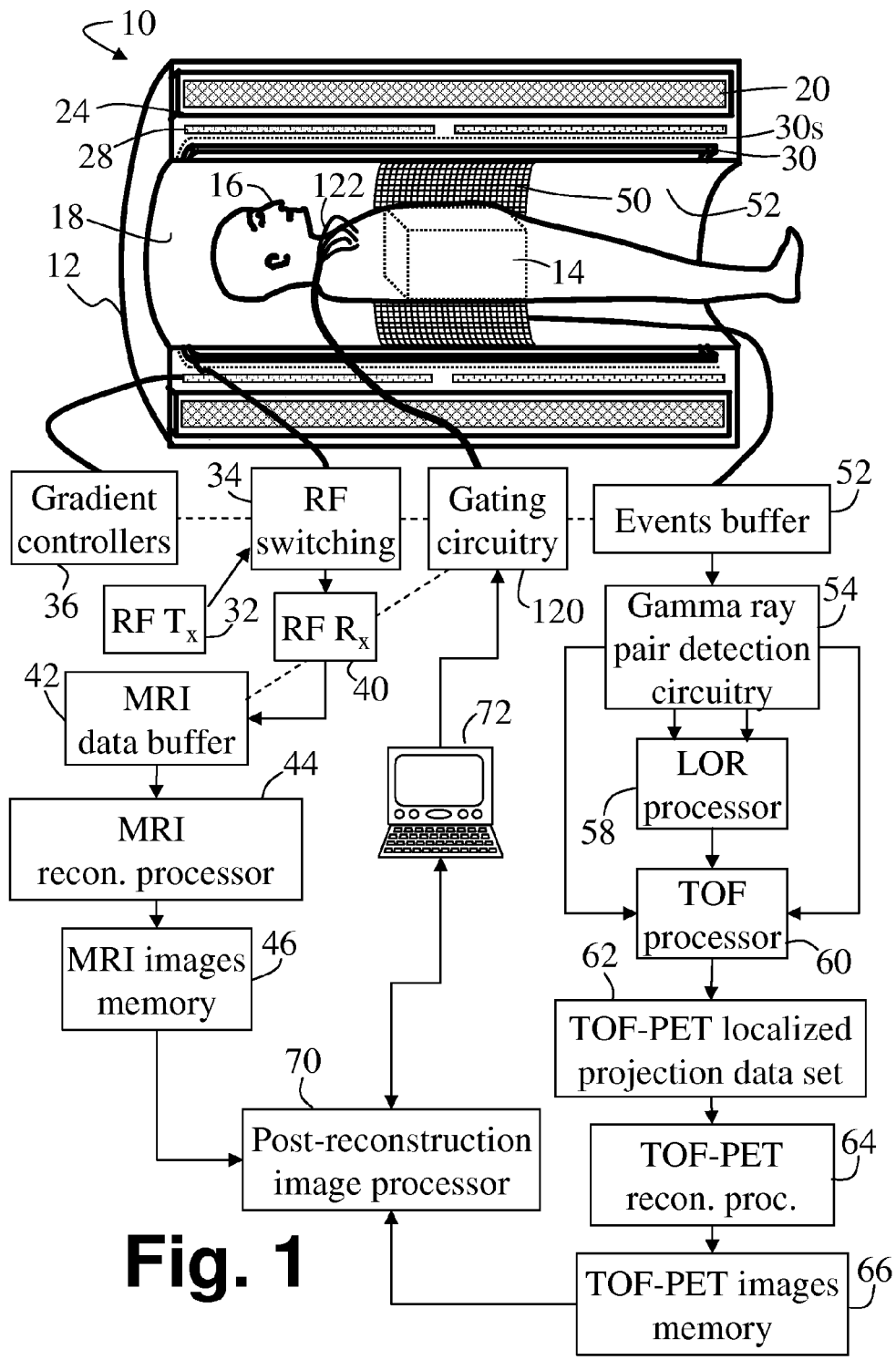

With reference to FIG. 1, a combined positron emission tomography/magnetic resonance imaging (PET/MRI) scanner 10 includes a common scanner housing 12 defining an imaging region 14 (indicated in phantom in FIG. 1) in which is disposed a patient or other imaging subject 16. A cosmetic bore liner 18 of the scanner housing 12 lines a cylindrical bore or opening of the housing 14 inside of which the imaging subject 16 is disposed. A main magnet 20 disposed in the housing 12 generates a main magnetic field in the imaging region 14. Typically, the main magnet 20 is a superconducting magnet surrounded by cryoshrouding 24; however, a resistive main magnet can also be used. Magnetic field gradient coils 28 are arranged in or on the housing 12 to superimpose selected magnetic field gradients on the main magnetic field within the imaging region 14. Typically, the magnetic field gradient coils include coils for producing three orthogonal magnetic field gradients, such as x-gradients, y-gradients, and z-gradients. In some embodiments, a whole-body radio frequency coil 30 with radio frequency screen 30s is arranged in or on the housing 12 to inject radio frequency excitation pulses into the imaging region 14. In other embodiments, one or more local coils (not shown) are used to inject the radio frequency excitation pulses.

During MRI data acquisition, a radio frequency transmitter 32 is coupled to the whole body coil 30 through radio frequency switching circuitry 34 as illustrated, or coupled to one or more local coils, to generate magnetic resonances at least in that portion of the imaging subject 16 disposed in the imaging region 14. A gradients controller 36 operates the magnetic field gradient coils 28 to spatially encode the magnetic resonances. For example, a one-dimensional magnetic field gradient applied during radio frequency excitation produces slice-selective excitation; magnetic field gradients applied between excitation and readout of magnetic resonances provide phase encoding; and magnetic field gradients applied during readout of magnetic resonances provide frequency encoding. The MRI pulse sequences can be configured to produce Cartesian, radial, spiral, or other spatial encodings.

After the radio frequency excitation, the switching circuitry 34 operatively disconnects the radio frequency transmitter 32 and operatively connects a radio frequency receiver 40 to the whole-body coil 30 (or, alternatively, the receiver 40 is connected to a local coil (not shown)) to acquire spatially encoded magnetic resonances from within the imaging region 14. The acquired spatially encoded magnetic resonances are stored in an MRI data buffer 42, and are reconstructed by an MRI reconstruction processor 44 to produce a reconstructed MRI image that is stored in an MRI images memory 46. The MRI reconstruction processor 44 employs a reconstruction algorithm that suitably decodes the spatially encoded magnetic resonances. For example, if Cartesian encoding is employed, a fast Fourier transform (FFT) reconstruction algorithm is suitable.

The combined PET/MRI scanner 10 further includes PET imaging capability via a plurality of solid state radiation detectors 50 arranged to detect gamma rays emitted from the imaging region 14. In the embodiment of FIG. 1, the radiation detectors 50 are disposed on the bore liner 18; however, the radiation detectors 50 can be located elsewhere in the scanner 10 (for other example placements of the radiation detectors 50, see FIGS. 7 and 8). In PET imaging, a positron-emitting radiopharmaceutical is administered to the imaging subject 16. Each emitted positron annihilates with an electron to produce two oppositely directed 511 keV gamma rays that are detected by the solid state radiation detectors 50. In FIG. 1, the plurality of solid state radiation detectors 10 are arranged as a plurality of detector rings; however, other arrangements of radiation detectors can be used.

Radiation detection events are stored in an events buffer 52, preferably in a list mode. Each stored radiation event typically includes an energy value and a timestamp indicative of when the radiation event was detected. Optionally, selected data processing is performed on the radiation detection events; for example, Anger logic processing can be applied to estimate the energy of the detected particle and to localize the position of the radiation detection event on the detector. Such Anger or other data processing can be performed using circuitry integrated with the radiation detectors 50, or can be performed after porting the detector signal off the detectors 50 (for example, in electronics associated with the events buffer 52).

Gamma ray pair detection circuitry 54 processes the radiation detection events to identify pairs of substantially simultaneous gamma ray detections belonging to single electron-positron annihilation events. The processing for identifying a pair of gamma rays emanating from a single positron-electron annihilation event can include, for example, energy windowing (that is, discarding radiation detection events outside of a selected energy filtering window disposed about 511 keV) and coincidence-detecting circuitry (that is, discarding radiation detection event pairs temporally separated from each other by greater than a selected time filtering interval). When a gamma ray pair is identified as substantially coincident, a line-of-response (LOR) processor 58 processes the spatial information pertaining to the two gamma ray detection events to identify a spatial line of response (LOR) connecting the two gamma ray detections. Since the two gamma rays emitted by a positron-electron annihilation event are oppositely spatially directed, the electron-positron annihilation event is known to have occurred somewhere along the LOR.

In TOF-PET, the radiation detectors 50 have sufficiently high temporal resolution to detect a time-of-flight difference between the two "substantially simultaneous" gamma ray detections. Accordingly, a time-of-flight processor 60 analyzes the time difference between the timestamps of the two gamma ray detection events to localize the positron-electron annihilation event along the LOR. The time-of-flight processor 60 localizes the LOR within a distance interval corresponding to about the speed of light times the temporal resolution of the radiation detectors 50. The result, accumulated for a large number of positron-electron annihilation events, is a set of localized projection data 62. A TOF-PET reconstruction processor 64 reconstructs the localized projection data 62 into a reconstructed image using any suitable reconstruction algorithm, such as filtered backprojection or iterative reconstruction with correction. The resulting reconstructed image is stored in a TOF-PET images memory 66. Because the reconstruction employs localized projection data that is at least partially localized along the LOR by the TOF information, the reconstruction is substantially less noisy than conventional PET image reconstruction which processes LORs extending fully between the two gamma ray detections.

The TOF-PET images and the MRI images can be aligned, commonly scaled and oriented, combined, superimposed, compared side-by-side, or otherwise integrated by a post-reconstruction image processor 70. The combined, superimposed, side-by-side, or otherwise integrated TOF-PET and MRI images are displayed on a user interface 72, printed, stored, communicated over an intranet or the Internet, or otherwise used. In some embodiments, the post-reconstruction image processor 70 uses a post-reconstruction image processing algorithm configured to be operable on either the PET image or the MRI image, or both. In some embodiments, the MRI and TOF-PET reconstruction processors 44, 64 output reconstructed images using the same image format, so that the post-reconstruction image processor 70 can process either type of image without performing image format conversion operations.

Optionally, the acquired localized projections and the acquired spatially encoded magnetic resonance data are tagged with time stamp information and inserted into a common data stream, such as a "list mode" data stream. The resulting reconstructed TOF-PET and MRI images can then be temporally aligned. Such temporal alignment can be useful for correction of dynamic data, providing morphological background for molecular imaging (compartment modeling), and so forth. Intermediate MRI images of moving objects can also be obtained through interpolation of time-stamped magnetic resonance data.

Figure 2:
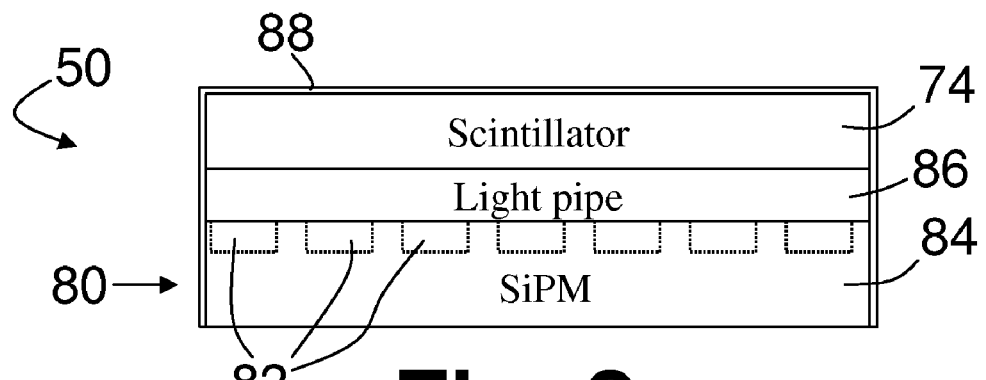

With reference to FIG. 2, each solid state radiation detector 50 includes a scintillator 74 that produces a scintillation or burst of light when a gamma ray is stopped by the scintillator 74. The burst of light is received by a solid state silicon photomultiplier (SiPM) 80 that includes an array of detector pixels 82 monolithically disposed on a silicon substrate 84. The SiPM 80 is advantageously fast enough to perform TOF-PET imaging, and additionally is substantially unaffected by the main magnetic field produced by the main magnet 20 of the MRI scanner portion. Typical SiPM devices have a temporal resolution of less than one nanosecond. The scintillator 74 is selected to provide high stopping power for 511 keV gamma rays with rapid temporal decay of the scintillation burst. Some suitable scintillator materials are LYSO and LaBr. Although FIG. 2 shows the scintillator 74 as a single crystal, an array of scintillator crystals can instead be used. Additionally, an optional planar light pipe 86 can be interposed between the scintillator 74 and the SiPM 80 to improve transmission of photons or to distribute the light of one scintillation pulse over more than one SiPM pixels. The scintillator 74 and optional light pipe 86 are optionally encased in a reflective coating 88 which directs scintillation light toward the SiPM 80.

Figure 3:
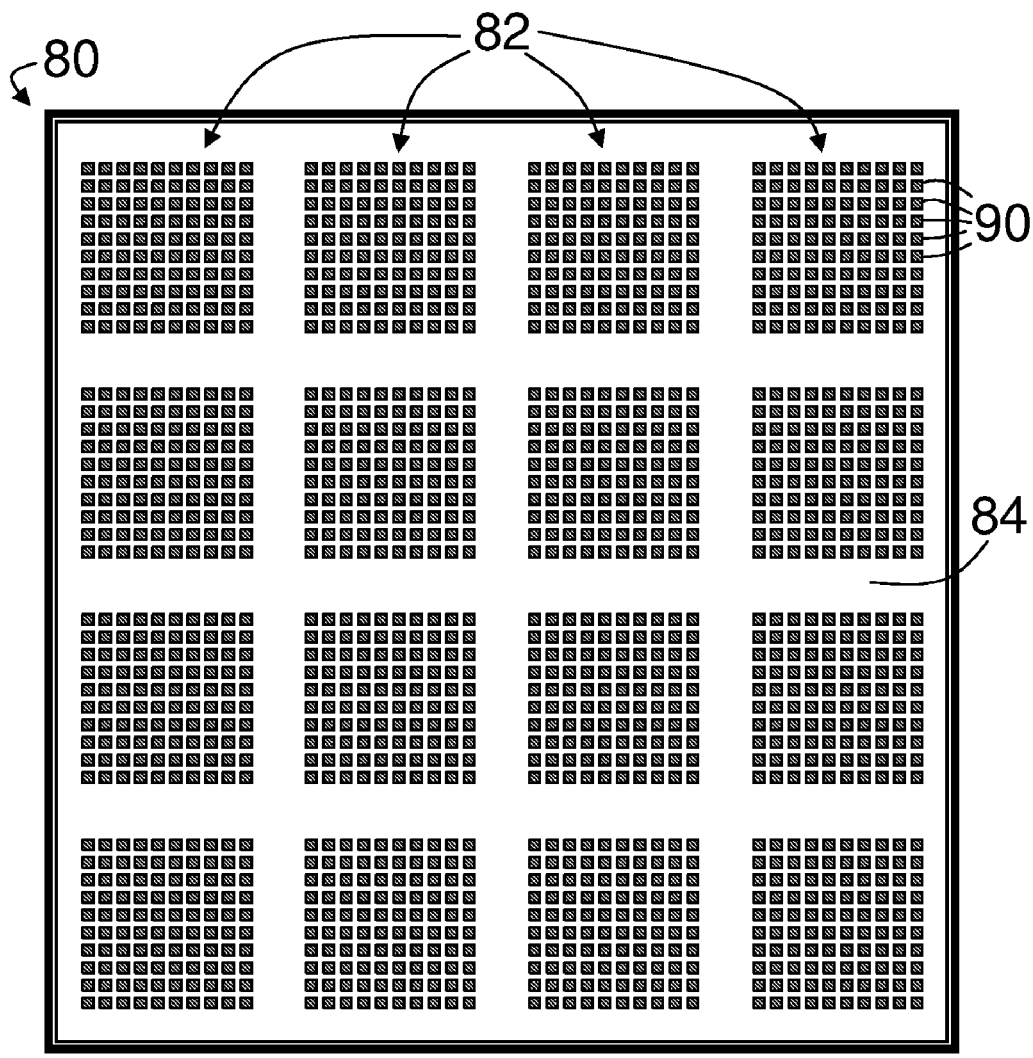

With continuing reference to FIG. 2 and with further reference to FIG. 3, each pixel 82 of the SiPM 80 includes an array of avalanche photodiodes 90 each biased in a breakdown region. The photodiodes 90 are suitably operated in a Geiger-mode type of operation, and conduct limited electrical current until a photon is absorbed or detected by the photodiode 90 and induces junction breakdown. When a photodiode 90 breaks down responsive to a photon detection, it conducts a large current limited by biasing circuitry. The photodiodes thus operate as "on-off" switches; each photodiode is "off" until it detects a photon, which turns it "on" to conduct current. FIG. 3 diagrammatically shows a 4×4 array of pixels 82, with each pixel 82 including a 10×10 array of photodiodes 90; however, larger arrays of pixels, each including larger arrays of photodiodes, suitably provide higher spatial resolution. For example, in some contemplated embodiments each pixel includes $10^3$-$10^4$ photodiodes. Typically, each photodiode 90 includes a guard ring (not shown) around the periphery that prevents avalanche breakdown at the edges of the photodiode 90. The guard ring structure suitably acts like an ordinary reverse-biased PN diode with internal fields too low for the avalanche breakdown to occur.

In some embodiments, the currents conducted by the photodiodes 90 of each pixel 82 are combined in analog fashion to produce an analog pixel output corresponding to a sum or other combination of the photodiode currents. Since each photodiode in the electrically conductive breakdown state has detected a photon, the analog sum of the photodiode currents corresponds to the number of photons detected by the pixel 82, which in turn corresponds to the intensity of the scintillation burst of light at the pixel 82. Such analog SiPM devices are described, for example, in: E. A. Georgievskya et al., "The solid state silicon photomultiplier for a wide range of applications", $17^{th}$ Int'l Conf. on Photoelectronics and Night Vision Devices, Proceedings of SPIE vol. 5126 (2003); and Golovin et al., "Novel type of avalanche photodetector with Geiger mode operation", Nuclear Instruments & Methods in Physical Research A, volume 518, pages 560-64 (2004).

Figure 4:
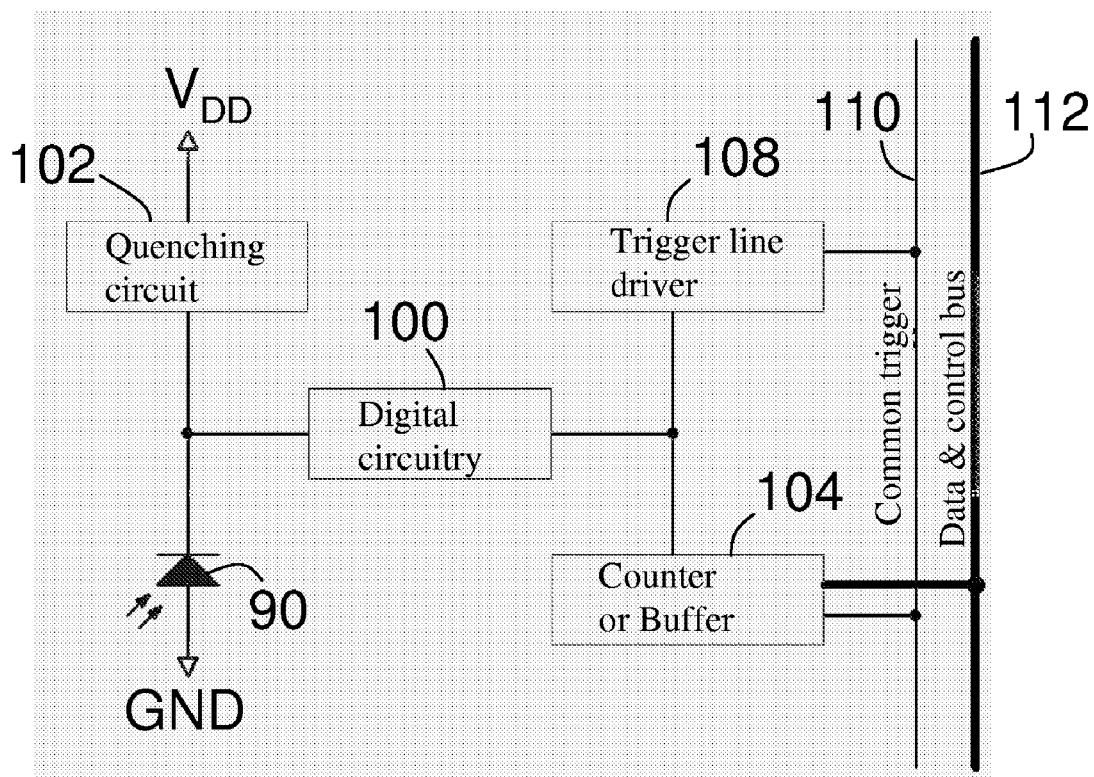
FIG. 4 shows an equivalent circuit of circuitry associated with one of the avalanche photodiodes of one of the pixels of a digital silicon photomultiplier.

With reference to FIG. 4, in other embodiments the SiPM is a digital device in which each photodiode 90 operates in a Geiger mode and is coupled with associated thresholding digital circuitry 100 that produces a first binary digital value when the photodiode 90 is biased in a quiescent state by a bias voltage ($V_{DD}$), and a second binary digital value when the photodiode 90 transitions into the conductive breakdown state. Because a digital value is output, the light intensity received by a pixel 82 can be estimated by digitally counting the number of photodiodes of the pixel 82 having associated digital circuitry 100 transitioned to the second digital value, rather than by generating an analog sum of photodiode currents.

With continuing reference to FIG. 4, when a photon strikes the photodiode 90, avalanche breakdown occurs, causing a large current to flow through the photodiode 90. When the photodiode 90 breaks down, large amount of charge (for example, about $10^6$ electrons per photon detection in some avalanche photodiodes) is generated through the avalanche breakdown process. This charge is transported primarily through a quenching circuit 102, which has an effective resistance of typically several hundred kilo-ohms to limit the current flowing through the photodiode 52. In some embodiments, the quenching circuit 102 is a resistor, typically in the kilo-ohm to mega-ohm range. In other embodiments, an active quenching circuit is employed. The current flow in the breakdown state changes an input voltage or current of the associated digital circuitry 100 to cause the digital circuitry 100 to transition from the quiescent first binary digital output value to the activated second binary digital output value. Moreover, with the current limited by the quenching circuit 102, charge remaining in the photodiode 90 distributes spatially to reduce the electric field in the avalanche region of the photodiode 90. This screening quenches the avalanche process and causes remaining carriers to be transported by drift out of the avalanche/depletion zone, causing quenching of the avalanche breakdown and recovery of the photodiode 90.

A digital buffer or counter 104 coupled with the digital circuitry 100 counts each transition from the first binary digital state to the second binary digital state. That is, the digital buffer or counter 104 counts photons absorbed by the associated photodiode 90. A trigger line driver 108 coupled with the digital circuitry 100 causes a common trigger line 110 (common to all the photodiodes 90 of a given pixel 82) to be set when a photon is detected. Pixel-level digital circuitry (not shown) initiates a count of binary transitions of the photodiodes 90 of the pixel 82 over an integration time period initiated by the first received photon causing the common trigger line 108 to be set. The resulting count over the integration time period indicates the intensity of light received by the pixel 82 in terms of an absorbed photon count. The final photon count is communicated off-chip by a data and control bus 112. In some embodiments, the digital buffer or counter 104 is a latch-type buffer that holds the second binary digital state in order for it to be counted. In such embodiments, each photodiode 90 can count only a single photon over the integration time period, and the latch buffers are reset at the end of the integration period by pixel-level digital circuitry. In other embodiments, the digital buffer or counter 104 is a digital counter which can count multiple photons detected by the associated photodiode 90, so long as the photodiode 90 is quenched back to its quiescent state by the quenching circuit 102 between received photons. The digital SiPM is suitably implemented using CMOS digital logic in conjunction with silicon avalanche photodiodes.

The SiPM devices 80 (whether analog or digital) are substantially unaffected by the main magnetic field produced by the main magnet 20. However, the magnetic field gradients produced by the gradient coils 30 of the MRI scanner portion may induce heating, eddy currents in conductive metal traces, or other transient effects that may detrimentally affect acquisition of TOF-PET data using the solid state radiation detectors 50.

With reference to FIG. 1, gating circuitry 120 optionally prevents collection of data from the plurality of solid state radiation detectors 50 when the magnetic field gradient coils 28 are operating. For example, in some embodiments the gating circuitry 120 detects energizing of one or more of the magnetic field gradient coils 28 and in response generates an inhibit signal that prevents collection or storage of radiation detection events output by the detectors 50. When the magnetic field gradient is removed, the gating circuitry 120 removes the inhibit signal, thus allowing collection of radiation detection events to resume.

For cardiac imaging, the gating circuitry 120 is optionally configured to monitor the cardiac cycle using an electrocardiograph 122 or other heart monitor. The gating circuitry 120 provides timing signals for both the MRI and TOF-PET scanner portions of the PET/MRI scanner 10 so as to ensure that the TOF-PET imaging and the MRI imaging each acquire data during different, selected portions of the cardiac cycle. Other physiological functions can be similarly gated, such as respiration. Physiological gating again prevents magnetic field gradients generated during the MRI imaging portion from interfering with the TOF-PET imaging. Moreover, gating by physiological state can direct the TOF-PET imaging portion to a functionally interesting transient portion of the physiological cycle, with the MRI imaging portion relegated to a quieter portion of the physiological cycle in which morphological features are relatively unchanging.

In some embodiments, the gating is performed retroactively. Both MRI and TOF-PET data are acquired continuously, and the gating circuitry 120 tags or annotates the data as to cardiac state, respiration state, applied magnetic field gradient, radio frequency excitation, or another gating parameter or plurality of parameters. The annotations are stored along with the data in the buffers 42, 52. During image reconstruction, data can be selectively filtered such that, for example, only TOF-PET data acquired during a selected portion of the cardiac cycle is reconstructed.

Figure 5:
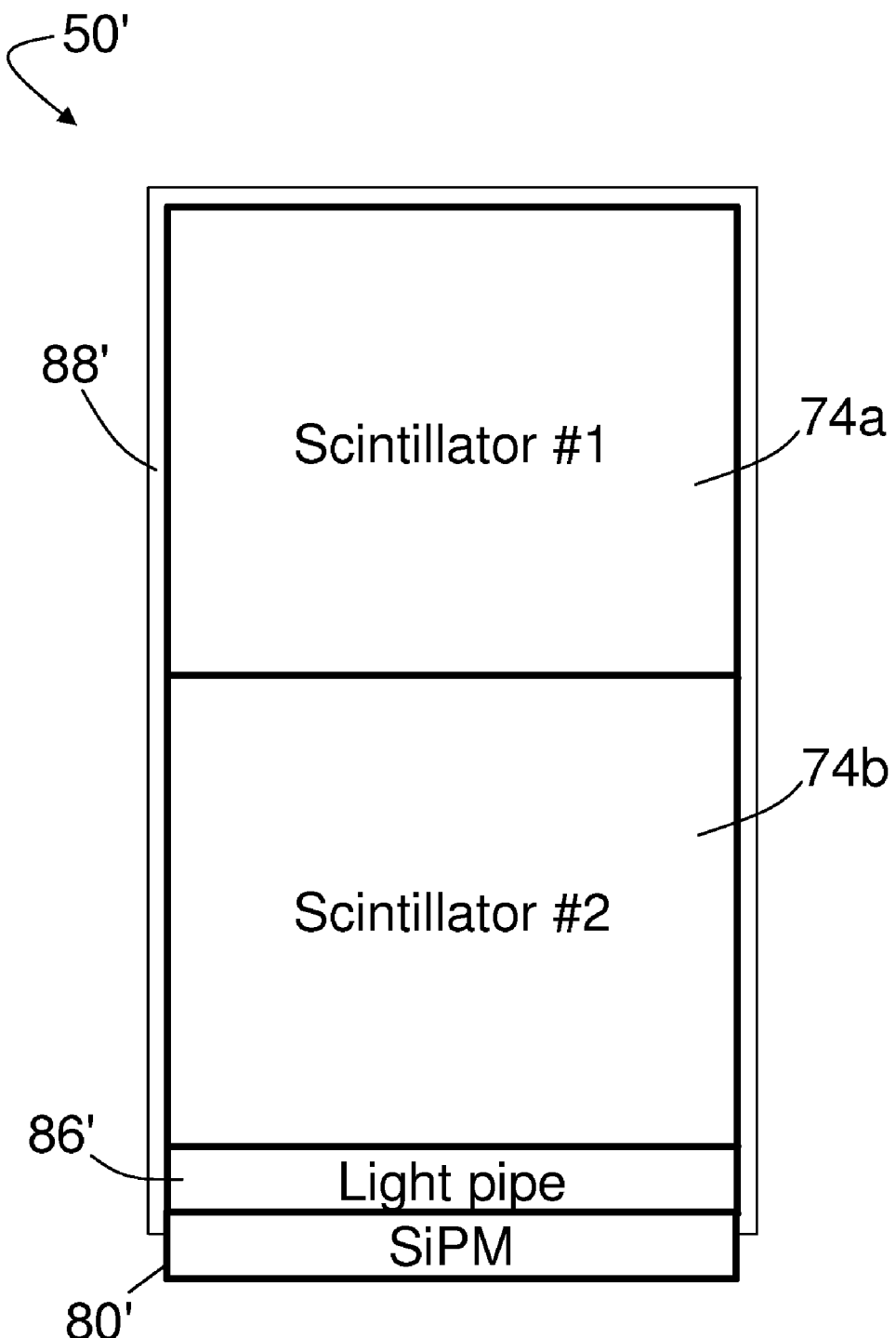
FIG. 5 shows a solid state radiation detector with a silicon photomultiplier and a plurality of scintillators to provide depth of interaction information.

With reference to FIG. 5, TOF-PET resolution can be further increased by providing a mechanism for determining the depth-of-interaction of radiation detection events. FIG. 5 illustrates one approach. A solid state radiation detector 50' includes two scintillators 74a, 74b stacked such that the first scintillator 74a is closest to the imaging region 14 while the second scintillator 74b is further away from the imaging region 14. The scintillators 74a, 74b have a detectably different optical characteristic, such as a different scintillation rise time or decay time, different emitted photon energy, or so forth. A SiPM 80' (which is substantially the same as the SiPM 80 of FIG. 2) is optically coupled with the scintillators 74a, 74b via a planar light pipe 86' to receive scintillation bursts of light from either of the scintillators 74a, 74b. The depth of interaction is determined by whether the first scintillator 74a or the second scintillator 74b produced the gamma ray detection, as indicated by the detectably different optical characteristics of scintillations produced by the two scintillators 74a, 74b.

The illustrated detector 50' includes two scintillators 74a, 74b, which provides two-level depth-of-interaction information. Three-level or higher level depth-of-interaction information can in principle be provided by stacking three or more scintillators. However, stacking three or more scintillators in accordance with the arrangement of FIG. 5 has certain difficulties. Each scintillator must have an optical characteristic that is detectably distinguishable from the other scintillators of the stack. Additionally, light from the scintillator closest to the imaging region 14 must pass through all the intervening scintillators to reach the SiPM 80', which can lead to optical losses or scattering and concomitant loss of energy and/or temporal resolution. Providing a reflective coating 88' (similar to the reflective coating 88 of FIG. 2, covering both scintillators 74a, 74b) can improve light collection, but optical losses or scattering at the interface of the dissimilar scintillators 74a, 74b may still be a problem.

In some contemplated embodiments, the levels of scintillators providing depth-of-interaction information are relatively offset laterally by a fractional pixel pitch (for example, two layers of scintillator pixels relatively offset by one-half of the pixel pitch). In this arrangement, the offset layers of scintillator pixels are read out by the SiPM coupled through a light pipe using Anger logic.

Figure 6:
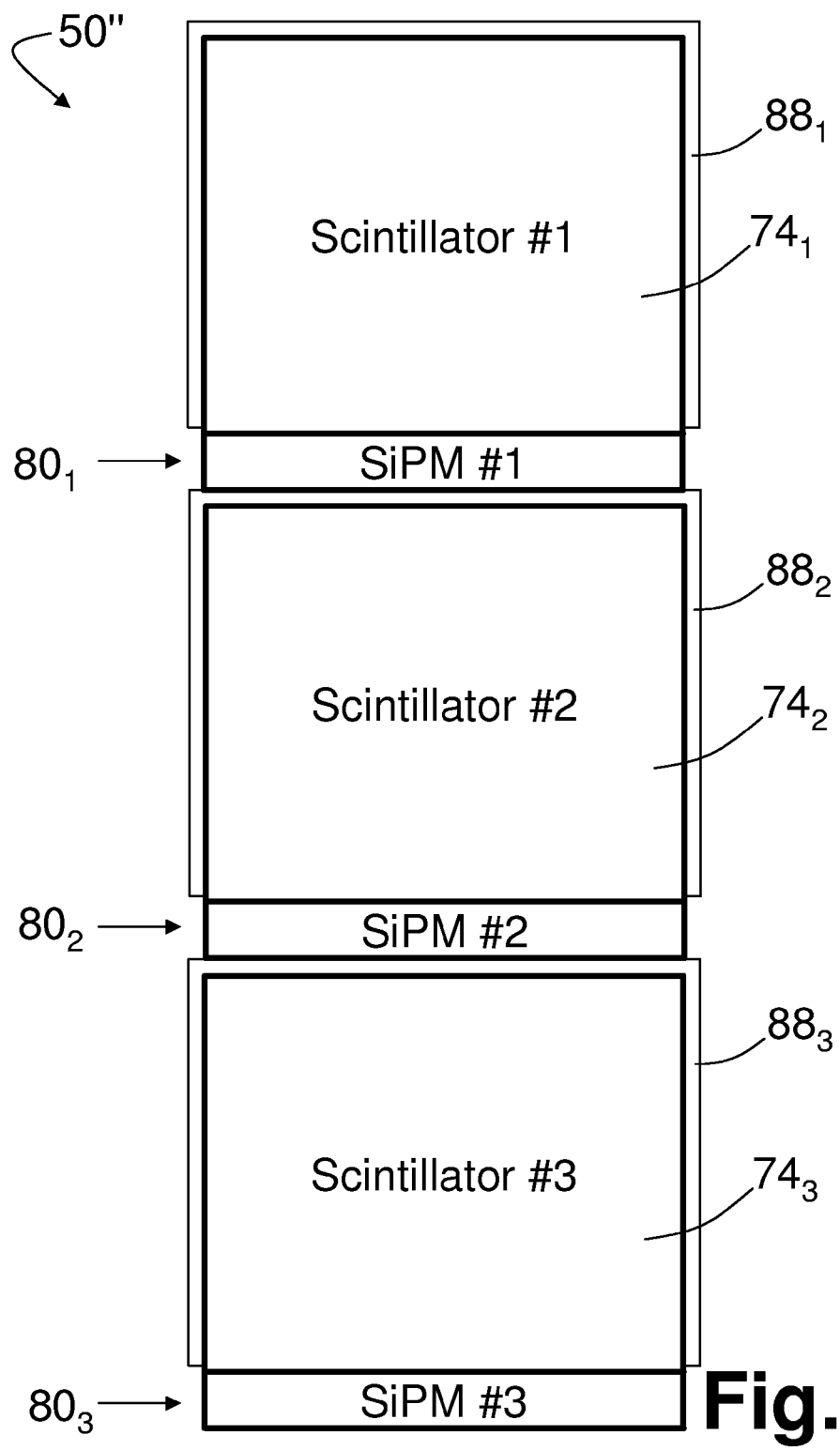
FIG. 6 shows a solid state radiation detector with a plurality of scintillators and a corresponding plurality of silicon photomultipliers to provide depth of interaction information without requiring different types of scintillators.

With reference to FIG. 6, an alternative approach for achieving depth-of-resolution is described, which takes advantage of the relative thinness and consequent radiation transparency of the SiPM detectors. A solid state radiation detector 50" includes three scintillators $74_1$, $74_2$, $74_3$ stacked such that the first scintillator $74_1$ is closest to the imaging region 14, the third scintillator $74_3$ is furthest from the imaging region 14, and the second scintillator $74_2$ is disposed between the first and third scintillators $74_1$, $74_3$. The scintillators $74_1$, $74_2$, $74_3$ can be of the same type, because there is no need for each scintillator to have a detectably different optical characteristic. The scintillator $74_1$ is optically coupled with a first SiPM $80_1$ disposed between the first and second scintillators $74_1$, $74_2$ with its light-sensitive surface facing the first scintillator $74_1$. A reflective coating $88_1$ coats the first scintillator $74_1$. Thus, photons generated in the first scintillator $74_1$ are directed to the first SiPM $80_1$, where the photons are either detected or absorbed in the silicon substrate. (It is also contemplated to dispose a reflective coating on those portions of the silicon substrate not occupied by photodiodes, so as to recover some of the photons that strike the SiPM $80_1$ in areas not covered by photodiodes).

In a similar fashion, the scintillator $74_2$ is optically coupled with a second SiPM $80_2$ disposed between the second and third scintillators $74_2$, $74_3$ with its light-sensitive surface facing the second scintillator $74_2$. A reflective coating $88_2$ coats the second scintillator $74_2$ so that photons generated in the second scintillator $74_2$ are directed to the second SiPM $80_2$. The scintillator $74_3$ is optically coupled with a third SiPM $80_3$ disposed on the side of the scintillator $74_3$ distal from the second SiPM $80_2$ with its light-sensitive surface facing the third scintillator $74_3$. A reflective coating $88_3$ coats the third scintillator $74_3$ so that photons generated in the third scintillator $74_3$ are directed to the third SiPM $80_3$. Thus, each of the SiPM devices $80_1$, $80_2$, $80_3$ is optically coupled with only one corresponding scintillator $74_1$, $74_2$, $74_3$, enabling straightforward depth of interaction determination.

The stacked radiation detector 50" of FIG. 6 is enabled by the fact that the SiPM devices are sufficiently thin that gamma rays generally pass through the SiPM devices unimpeded. On the other hand, photons generated by scintillation events are absorbed by the substrate of the SiPM device, thus preventing crosstalk between the scintillator/SiPM units. In the stacked radiation detector 50", the SiPM devices $80_1$, $80_2$, $80_3$ are directly optically coupled with the corresponding scintillators $74_1$, $74_2$, $74_3$ without intervening light pipes; however, light pipes can also be included to improve the optical coupling. While a stack of three scintillators $74_1$, $74_2$, $74_3$ is illustrated (providing three-level depth-of-interaction resolution), the number of stacked scintillators can be two or more than three. Moreover, the SiPM devices can be arranged on the sides of the scintillators transverse to the gamma ray-receiving surfaces of the scintillators, or in other positions offering suitable optical coupling with the scintillators, rather than between the scintillators.

In FIG. 1, the radiation detectors 50 are disposed on the bore liner 18 of the PET/MRI) scanner 10. This arrangement provides an unimpeded line-of-sight between the detectors 50 and the imaging subject 16. However, the exposed detectors may be aesthetically unpleasing and prone to damage through contact with the imaging subject 16.

Figure 7:
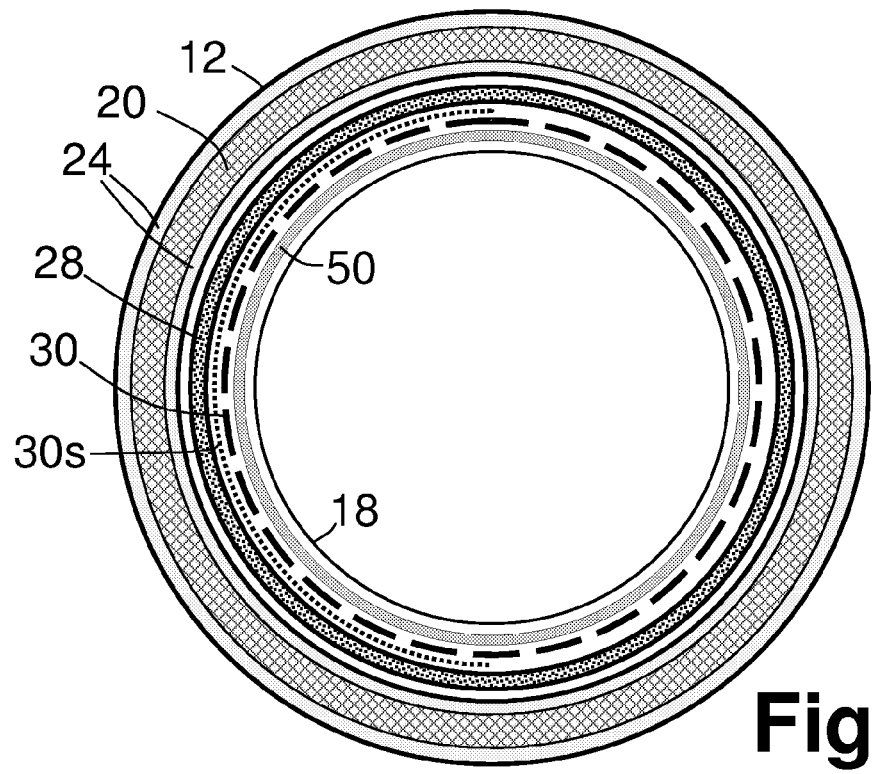
FIG. 7 shows a sectional end view of a TOF-PET/MRI scanner in which the solid state radiation detectors are covered by the bore liner of the housing.

With reference to FIG. 7, in some alternative embodiments the radiation detectors 50 are disposed inside of the bore liner 18, for example between the radio frequency coil 30 and the bore liner 18. This arrangement is generally more aesthetically pleasing, and provides protection for the radiation detectors 50. The bore liner 18 is generally made of plastic, fiberglass, or another material that is substantially transparent to 511 keV gamma rays; accordingly, placement of the radiation detectors 50 inside of the bore liner 18 is not expected to substantially reduce the radiation detection efficiency.

Figure 8:
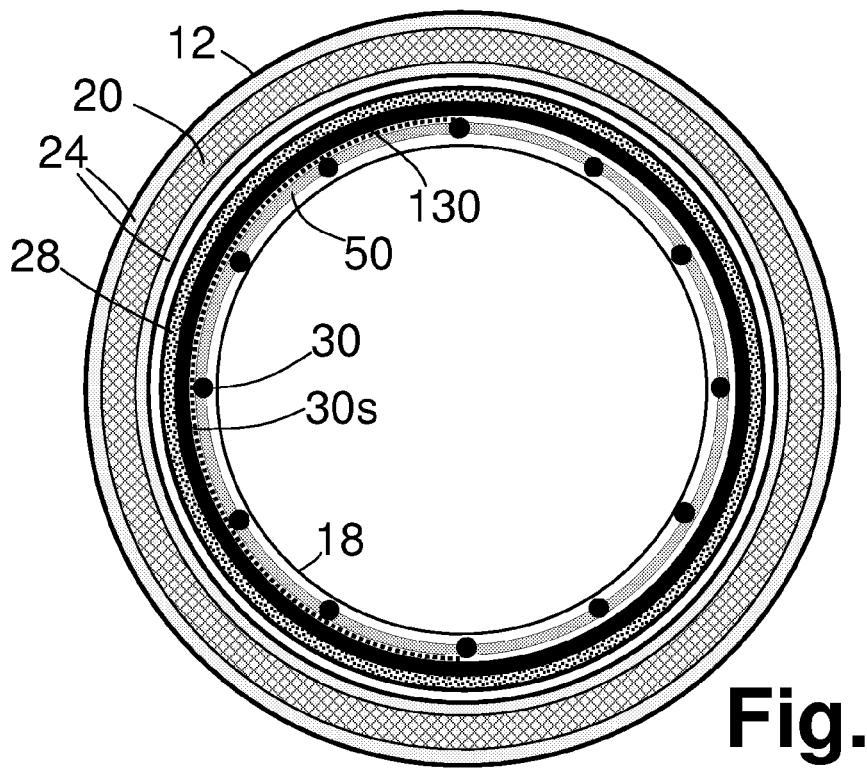
FIG. 8 shows a sectional end view of a TOF-PET/MRI scanner in which the solid state radiation detectors are disposed in gaps between the rungs of a birdcage coil of the MR portion of the scanner.

With reference to FIG. 8, in other alternative embodiments the radiation detectors 50 are disposed further into the housing 12. In the embodiment of FIG. 8, the radio frequency coil 30 is embodied as a twelve-rung birdcage coil, and the plurality of solid state radiation detectors 50 are disposed at about the same radius as the radio frequency coil 30 in gaps between the rungs. This arrangement makes efficient use of the limited space within the housing 12.

Additionally, an optional gradient coils cooling system 130 is thermally coupled with the magnetic field gradient coils 28 to cool the magnetic field gradient coils 28. Because of their arrangement in close proximity with the radio frequency coil 30, the solid state radiation detectors 50 are also thermally coupled with the gradient coils cooling system 130 to cool the solid state radiation detectors. In other embodiments, a cooling system for the main magnet 20 (such as the cryoshrouding 24) is similarly adapted to also provide cooling for the radiation detectors 50. It is to be appreciated that the cooling of the radiation detectors 50 can be substantially less than that of the gradient coils 28 or main magnet 20 while still being effective. A decrease of a few degrees in the temperature of the SiPM devices can substantially reduce dark currents.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. An imaging system comprising:
    a magnetic resonance imaging scanner including at least a main magnet and magnetic field gradient coils housed in or on a scanner housing acquires spatially encoded magnetic resonances in an imaging region;
    a plurality of solid state radiation detectors disposed in or on the scanner housing and arranged to detect gamma rays emitted from the imaging region;
    time of flight positron emission tomography (TOF-PET) processing configured to determine localized lines of response based on (i) locations of substantially simultaneous gamma ray detections output by the solid state radiation detectors and (ii) a time interval between said substantially simultaneous gamma ray detections;
    time of flight positron emission tomography (TOF-PET) reconstruction processing configured to reconstruct the localized lines of response to produce a TOF-PET image; and
    magnetic resonance imaging (MRI) reconstruction processing configured to reconstruct the acquired magnetic resonances to produce an MRI image.

2. The imaging system as set forth in claim 1, wherein the plurality of solid state detectors includes an array of silicon photomultipliers.

3. The imaging system as set forth in claim 1, wherein the solid state radiation detectors have a temporal resolution of less than one nanosecond.

4. The imaging system as set forth in claim 1, wherein each solid state radiation detector includes:
    one or more scintillators arranged to absorb gamma rays emitted from the imaging region; and
    one or more silicon photomultipliers arranged to detect light generated by the one or more scintillators, each silicon photomultiplier including a plurality of avalanche photodiodes biased in a Geiger mode of operation.

5. The imaging system as set forth in claim 4, wherein the avalanche photodiodes are arranged into groups defining pixels, each pixel outputting an analog signal corresponding to a combination of currents conducted by the group of avalanche photodiodes defining that pixel.

6. The imaging system as set forth in claim 4, wherein the avalanche photodiodes are arranged into groups defining pixels, and the silicon photomultiplier includes:
    digital circuitry associated with each avalanche photodiode, the digital circuitry making a digital transition responsive to detection of a photon by the associated avalanche photodiode;

trigger circuitry associated with each pixel configured to define an integration time period responsive to detection of photons by avalanche photodiodes of that pixel; and digital counting circuitry associated with each pixel configured to count transitions of the digital circuitry of that pixel over the integration time period.

7. The imaging system as set forth in claim 1, wherein each solid state radiation detector includes:

a plurality of stacked scintillators arranged to absorb gamma rays emitted from the imaging region; and one or more silicon photomultipliers arranged to detect light generated by the plurality of stacked scintillators;

the TOF-PET processing being configured to account for a depth of interaction indicated by which of the plurality of stacked scintillators produced the gamma ray detection.

8. The imaging system as set forth in claim 7, wherein the one or more silicon photomultipliers includes:

a silicon photomultiplier corresponding to each scintillator arranged to detect light generated by that scintillator and not by other scintillators, the TOF-PET processing being configured to determine the depth of interaction based on which of the silicon photomultipliers produced the gamma ray detection.

9. The imaging system as set forth in claim 8, wherein at least one of the silicon photomultipliers is interposed between its corresponding scintillator and another of the stacked scintillators.

10. The imaging system as set forth in claim 7, wherein each of the plurality of scintillators of the solid state radiation detector have detectably different optical characteristics, the TOF-PET processing being configured to determine the depth of interaction based on the detected optical characteristic of the gamma ray detection.

11. The imaging system as set forth in claim 1, further including:

gating circuitry preventing detecting of gamma rays emitted from the imaging region when the magnetic field gradient coils are operating.

12. The imaging system as set forth in claim 1, further including:

gating circuitry that monitors a physiological cycle and enables collection of magnetic resonances during a first portion of the physiological cycle and detecting of gamma rays emitted from the imaging region during a second portion of the physiological cycle.

13. The imaging system as set forth in claim 1, further including:

gating circuitry that retroactively gates at least one of the TOF-PET reconstruction processing and the MRI reconstruction processing based on one or more physiological or imaging parameters monitored during the imaging data acquisition.

14. The imaging system as set forth in claim 1, wherein the radiation detectors include:

a cooling system thermally coupled with at least one of the main magnet and the magnetic field gradient coils to cool said at least one of the main magnet and the magnetic field gradient coils, the plurality of solid state radiation detectors also being thermally coupled with the cooling system to cool the solid state radiation detectors.

15. The imaging system as set forth in claim 1, further including:

a post reconstruction image processor configured to process a selected one or both of (i) the TOF-PET image and (ii) the MRI image.

16. The imaging system as set forth in claim 15, wherein the post reconstruction image processor is configured to superimpose the TOF-PET and MRI images.

17. An imaging method comprising:

acquiring spatially encoded magnetic resonances from within an imaging region;

detecting gamma rays emitted from the imaging region wherein the detecting of gamma rays includes generating a burst of light corresponding to each gamma ray and digitally counting photons of the burst of light using a plurality of digitally interconnected avalanche photodiodes;

determining localized lines of response based on (i) locations of detections of substantially simultaneously detected gamma rays and (ii) a time interval between said detections of said substantially simultaneously detected gamma rays;

reconstructing the localized lines of response to produce a time of flight positron emission tomography (TOF-PET) image; and reconstructing the acquired spatially encoded magnetic resonances to produce a magnetic resonance imaging (MRI) image.

18. The imaging method as set forth in claim 17, wherein the detecting of gamma rays has a temporal resolution of less than one nanosecond, and the determining of localized lines of response localizes the line of response to a distance interval along the line of response corresponding to about the speed of light times the temporal resolution of the detecting.

19. The imaging method as set forth in claim 17, further including:

performing post reconstruction image processing one at least one of (i) the TOF-PET image and (ii) the MRI image using a post reconstruction image processing algorithm configured to be operable on either the PET image or the MRI image.

20. An imaging system comprising:

a magnetic resonance imaging scanner including at least a main magnet and magnetic field gradient coils housed in or on a scanner housing acquiring spatially encoded magnetic resonances in an imaging region;

a plurality of solid state radiation detectors disposed in or on the scanner housing and arranged to detect gamma rays emitted from the imaging region;

a cooling system thermally coupled with at least one of the main magnet and the magnetic field gradient coils to cool said at least one of the main magnet and the magnetic field gradient coils, and additionally thermally coupled with the plurality of solid state radiation detectors to cool the solid state radiation detectors;

coincidence processing configured to determine lines of response based on locations of substantially simultaneous gamma ray detections output by the solid state radiation detectors;

positron emission tomography (PET) reconstruction processing configured to reconstruct the lines of response to produce a PET image; and magnetic resonance imaging (MRI) reconstruction processing configured to reconstruct the acquired magnetic resonances to produce an MRI image.

* * * * *